United States Patent [19]

Clark et al.

[11] Patent Number: 5,258,378
[45] Date of Patent: Nov. 2, 1993

[54] PYRROLOAZEPINE COMPOUNDS USEFUL AS DOPAMINERGIC AGENTS

[75] Inventors: Barry P. Clark, Lower Froyle; Graham H. Timms, Camberley; David E. Tupper, Reading, all of United Kingdom

[73] Assignee: Lilly Industries Limited, Basingstoke, England

[21] Appl. No.: 794,283

[22] Filed: Nov. 19, 1991

[30] Foreign Application Priority Data

Nov. 28, 1990 [GB] United Kingdom ............... 9025890

[51] Int. Cl.$^5$ .................. A61K 31/55; C07D 487/04
[52] U.S. Cl. ........................... 514/215; 540/580
[58] Field of Search .................. 540/580; 514/215

[56] References Cited

U.S. PATENT DOCUMENTS

| | | | |
|---|---|---|---|
| 3,553,232 | 1/1971 | Hester, Jr. | 260/326.5 |
| 4,414,225 | 11/1983 | Sauter et al. | 424/274 |
| 4,575,504 | 3/1986 | Sauter et al. | 514/215 |
| 4,751,222 | 6/1988 | Brasstrup et al. | 514/213 |
| 4,904,653 | 2/1990 | Clark et al. | 514/215 |
| 5,028,602 | 2/1991 | Clark et al. | 514/215 |

FOREIGN PATENT DOCUMENTS 0028381 5/1981 European Pat. Off. .
0324610 7/1989 European Pat. Off. .

OTHER PUBLICATIONS

A. Barnett, *Drugs of the Future*, II, 49-56 (1986).
Anderson et al., *Eur. J. Pharmacol.* 137, 291-92 (1987).

*Primary Examiner*—Mukund J. Shah
*Assistant Examiner*—Philip Datlow
*Attorney, Agent, or Firm*—MaCharri R. Vorndran-Jones; Leroy Whitaker

[57] ABSTRACT

The invention relates to a compound of formula (I)

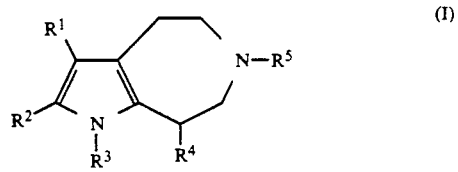

in which $R^1$ and $R^2$ are each hydrogen, halo, hydroxy, nitro, $C_{1-4}$ alkylcarbonyl, hydroxy-$C_{1-4}$ alkyl, $R^3$ is hydrogen or optionally substituted phenylsulphonyl, $R^4$ is optionally substituted phenyl, benzofuranyl or dihydrobenzofuranyl, and $R^5$ is hydrogen or $C_{1-4}$ alkyl; and salts thereof. These compounds are useful dopaminergic agents.

8 Claims, No Drawings

PYRROLOAZEPINE COMPOUNDS USEFUL AS DOPAMINERGIC AGENTS

This invention relates to novel chemical compounds and their use as pharmaceuticals.

The compounds of the invention have the formula

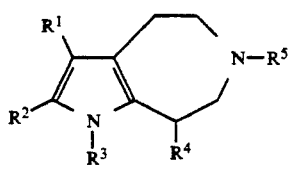

(I)

in which $R^1$ and $R^2$ are each hydrogen, halo, hydroxy, nitro, $C_{1-4}$ alkylcarbonyl, hydroxy-$C_{1-4}$ alkyl, $R^3$ is hydrogen or optionally substituted phenylsulphonyl, $R^4$ is optionally substituted phenyl, benzofuranyl or dihydrobenzofuranyl, and $R^5$ is hydrogen or $C_{1-4}$ alkyl; and salts thereof.

Compounds of the invention in which $R^1$ and $R^2$ are both hydrogen, and those in which $R^3$ is optionally substituted phenylsulphonyl are intermediates in the preparation of the remaining, biologically active, compounds which exhibit useful effects on the central nervous system.

When reference is made to halo, preferred groups are fluoro, chloro and bromo, especially chloro and bromo. A hydroxy-$C_{1-4}$ alkyl group is a $C_{1-4}$ alkyl group substituted by —OH and the $C_{1-4}$ alkyl group can be straight or branched, examples being methyl, ethyl, propyl, isopropyl and tert. butyl. Especially preferred examples of hydroxy-$C_{1-4}$ alkyl are —CH(CH$_3$)OH and —C(CH$_3$)$_2$OH. The group $R^1$ is preferably hydrogen or halo, and $R^2$ is also preferably hydrogen or halo.

The group $R^3$ is hydrogen or optionally substituted phenylsulphonyl, the latter being a protecting group useful for protecting the nitrogen during synthetic reactions. Optionally substituted phenyl can be phenyl or a phenyl group with one or more, such as one to three, substitutents selected from for example nitro, cyano, amino, hydroxyl, trifluoromethyl, $C_{1-4}$ alkyl, especially methyl, $C_{1-4}$ alkoxy, especially methoxy and ethoxy, and halogen especially fluorine, chlorine or bromine. Preferred substitutents are $C_{1-4}$ alkyl, $C_{1-4}$ alkoxy and halogen.

The group $R^4$ is optionally substituted phenyl, as defined above, or benzofuranyl or dihydrobenzofuranyl. Preferred examples are phenyl and

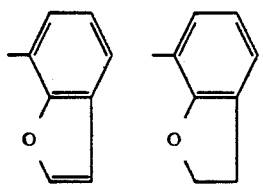

The group $R^5$ is $C_{1-4}$ alkyl, as defined above, or hydrogen, and is preferably methyl.

A preferred group of compounds is of formula (I) in which $R^1$ is halo and $R^2$ is hydrogen, or both $R^1$ and $R^2$ are halo, $R^3$ is hydrogen, $R^4$ is phenyl and $R^5$ is $C_{1-4}$ alkyl; and salts thereof.

The novel compounds are useful both in free amine form and as salts. The ring nitrogen atom is basic and furthermore there may be basic substituents on the molecule so the compounds can exist as acid addition salts. The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycolic, maleic, hydroxymaleic, fumaric, malic, tartaric, citric, salicyclic, o-acetoxybenzoic, nicotinic or isonicotinic acid, or organic sulphonic acids for example methane sulphonic, ethane sulphonic, 2-hydroxyethane sulphonic, toluene-p-sulphonic, or naphthalene-2-sulphonic acid.

In addition to pharmaceutically acceptable salts, other salts are also included in the invention such as, for example, those with picric or oxalic acids; they may serve as intermediates in the purification of the compounds or in the preparation of other, for example pharmaceutically acceptable, acid addition salts, or are useful for identification, characterisation or purification of the bases.

It will be appreciated that the compounds of formula (I) possess a chiral centre at the carbon atom of the nitrogen-containing ring to which the $R^4$ group is attached. All stereo-isomers, and racemic mixtures, thereof are included within the scope of the invention. Isomers can be isolated from racemic mixtures by conventional methods such as by preparing suitable salts with a chiral acid and subsequently liberating the enantiomers or, alternatively, they can be prepared by methods devised to give the pure isomer.

The invention also includes a process for preparing the compounds of formula (I), which comprises cyclising a compound of the formula

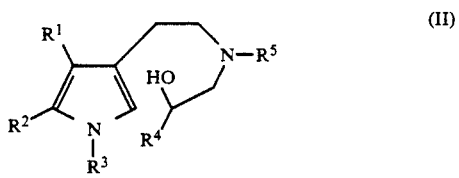

(II)

in which $R^1$, $R^2$, $R^4$ and $R^5$ have the values defined above, and $R^3$ is optionally substituted phenylsulphonyl, and optionally removing the $R^3$ protecting group or converting $R^1$, $R^2$ or $R^5$ to a desired substituent.

This cyclisation reaction is preferably carried out at a temperature of from 0° C. to 100° C. in the presence of an acid such as for example an alkane sulphonic acid, for instance methane sulphonic acid, and a trihaloacetic acid, for instance trifluoroacetic acid.

Compounds of formula (II) can be prepared from known nitroolefins of the formula

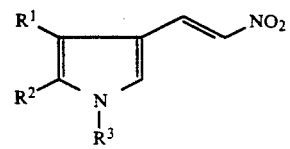

where $R^3$ is phenylsulphonyl, by a sequence of reactions involving, first of all, reduction to the corresponding amine:

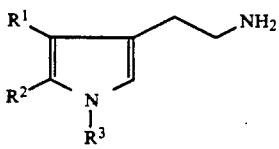

This amine can then be reacted with an oxirane of formula:

to give the intermediate compound of formula (II) in which $R^5$ is hydrogen.

Alternatively an amine of formula (III) can be alkylated by prior trifluoroacetylation of the amino group and alkylation of the amido compound formed, followed by the removal of the trifluoroacetyl group, according to well known procedures. Reaction of the product with an oxirane of formula (IV) gives the intermediate of formula (II) in which $R^5$ is $C_{1-4}$ alkyl.

Oxirane intermediates of formula (IV) are known compounds or can be prepared by standard methods such as for example from the appropriate aldehyde by use of sodium hydride and trimethyl sulphoxonium iodide in dimethyl sulphoxide.

It will be appreciated that compounds of formula (I) in which $R^1$ or $R^2$ is hydrogen or both $R^1$ and $R^2$ are hydrogen, can be converted to other compounds of formula (I) by for example acylation to give $C_{1-4}$ alkylcarbonyl derivatives and reduction by, for example, sodium borohydride or treatment with Grignard reagent to give hydroxy-$C_{1-4}$ alkyl derivatives. Halo derivatives can be prepared by halogenation of the protected compound, and lithiation of the halo derivative followed by treatment with a peroxide derivative yields the hydroxy derivative. The nitro derivatives can be prepared by well known nitration procedures.

A preferred process for producing compounds in which one or both of $R^1$ and $R^2$ are halo comprising halogenation, for example bromination, with excess halogen to give compounds of formula (I) in which both $R^1$ and $R^2$ are halogen, or halogenation with one mole of halogen to give a compound of formula (I) which is monohalogenated in the 2-position. The latter compounds can be rearranged to provide the 3-substituted monohalogenated analogue by acid catalysis as for example disclosed in Comprehensive Heterocyclic Chemistry by A. R. Katritzky and C. W. Rees, Vol. 4, Part 3, page 215.

As mentioned above, the compounds of formula (I), with the exception of those in which both $R^1$ and $R^2$ are hydrogen and those in which $R^3$ in optionally substituted phenylsulphonyl, have useful central nervous system activity with low toxicity. This activity has been demonstrated in extensive testing using well-established procedures. More specifically the compounds have been shown to have activity in the $^3$H—SCH23390 binding test described by Billard et al., Life Sciences, Volume 35, pages 1885–1893, 1984. For example, the compounds of Examples 10 and 12 have an $IC_{50}$ value (the concentration of the compound required to reduce the binding of $^3$H—SCH23390 by 50%) of 1.1 and 0.15 μM, respectively. This test indicates that the compounds interact with dopamine, $D_1$ receptors in the central nervous system and this is confirmed by their ability to alter the production of cyclic adenosine monophosphate by rat retinal homogenates (Riggs et al., J. Med. Chem., Volume 30, pages 1914–1918, 1987). The compounds of formula (I) and pharmaceutically-acceptable acid addition salts thereof, are potent centrally acting compounds which are useful in the treatment of depression, mild anxiety states, certain kinds of psychotic conditions such as schizophrenia and acute mania and parkinsonism.

The invention also includes a pharmaceutically composition comprising a pharmaceutically acceptable diluent or carrier in association with a biologically-active compound of formula (I) in unprotected form; or a pharmaceutically acceptable salt thereof.

The compounds may be administered by various routes, for example by the oral or rectal route, topically or parenterally, for example by injection, and by inhalation, being usually employed in the form of a pharmaceutical composition. Such compositions are prepared in a manner well known in the pharmaceutical art and normally comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatine, syrup, methyl cellulose, methyl- and propyl- hydroxybenzoate, talc, magnesium sterate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example, from 25 mg to 200 mg. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The invention is illustrated by the following Examples. The structure of the compounds prepared was confirmed by nuclear magnetic resonance, infra-red, and mass spectra and the purity of the product was checked in most cases by HPLC. The reactions described give racemic mixtures.

EXAMPLE 1

2-(1-Phenylsulphonyl-3-pyrrolyl)ethylamine

Boron trifluoride etherate (17.7 g) was added under nitrogen with ice-cooling to sodium borohydride (3.94 g) suspended in tetrahydrofuran (150 ml). After stirring at room temperature for fifteen minutes 2-(1-phenylsulphonyl-3-pyrrolyl)-1-nitroethylene (5.78 g) (prepared according to Synthetic Communications, 15 (1), 71–74 (1985)), dissolved in tetrahydrofuran (80 ml) was added dropwise. The mixture was refluxed overnight, quenched by the addition of ice-water, acidified with 5M hydrochloric acid and refluxed for a further two hours. The aqueous layer was washed with ether and the amine liberated by the addition of 0.880 ammonia solution which was extracted into dichloromethane. The extracts were washed with water, dried and evaporated to give pure product as an oil.

EXAMPLE 2

N-Trifluoroacetyl-2-(1-phenylsulphonyl-3-pyrrolyl)ethylamine

Trifluoroacetic anhydride (4.37 g) was added dropwise to an ice-cooled solution of 2-(1-phenylsulphonyl-3-pyrrolyl)ethylamine (4.54 g) and triethylamine (5.51 g) in dichloromethane (50 ml). The solution was evaporated to dryness, then 2M hydrochloric acid (50 ml) was added and the product was extracted into ether. The ether was washed with water, dried and evaporated to give a brown oil which was purified by chromatography on silica eluting with increasing amounts of methanol (1→20%) in chloroform to give the title product as a brown oil.

EXAMPLE 3

N-Methyl-2-(1-phenylsulphonyl-3-pyrrolyl)ethylamine

50% Sodium hydride oil dispersion (0.62 g) was added to an ice-cooled solution of N-trifluoroacetyl-2-(1-phenylsulphonyl-3-pyrrolyl)ethylamine (3.59 g) in dimethylformamide (20 ml) after 20 minutes, methyl iodide (1.76 g) was added and the mixture was heated at 70° C. overnight. After cooling, water was added and the mixture was extracted with ether 3 times. The ether was washed with water, dried and evaporated to give N-methyl-N-trifluoroacetyl-2-(1-phenylsulphonyl-3-pyrrolyl)ethylamine as an oil. The oil was dissolved in methanol (40 ml), 0.880 ammonia added and the solution was stirred for 6 hours. After evaporation, the residue was dissolved in 5M hydrochloric acid and extracted with ether. The aqueous part was basified with 0.880 ammonia and the product was extracted into dichloromethane. The extracts were washed with water, dried and evaporated to give the title product as a pure oil.

EXAMPLE 4

N-(2-Hydroxy-2-phenylethyl)-2-(1-phenylsulphonyl-3-pyrrolyl)ethylamine

A mixture of 2-(1-phenylsulphonyl-3-pyrrolyl)ethylamine (1.8 g), styrene oxide (0.51 g) and acetonitrile (20 ml) were refluxed for three days. The solution was evaporated and the brown oil was purified by chromatography on silica, eluting with dichloromethane, chloroform then with increasing amounts of methanol (1→10%) in chloroform, to give the title product as a brown oil.

EXAMPLE 5

N-(2-Hydroxy-2-phenylethyl)-N-methyl-2-(1-phenylsulphonyl-3-pyrrolyl)ethylamine

A mixture of N-methyl-2-(1-phenylsulphonyl-3-pyrrolyl)ethylamine (4 g), styrene oxide (2.06 g) and acetonitrile (50 ml) were refluxed for 2 days. The solution was evaporated and the brown oil was purified by chromatography on silica, eluting with dichloromethane, chloroform then with increasing amounts of methanol (1→25%) in chloroform to give the title product as a brown oil.

EXAMPLE 6

1-Phenylsulphonyl-1,4,5,6,7,8-hexahydro-8-phenylpyrrolo[2,3-d]azepine

N-(2-Hydroxy-2-phenylethyl)-2-(1-phenylsulphonyl-3-pyrrolyl)ethylamine (1.67 g), trifluoroacetic acid (60 ml) and methanesulphonic acid (0.65 g, 6.68 mmole) were refluxed for 1.5 hours. After evaporating to dryness, water then 0.88 ammonia were added and the product was extracted into dichloromethane. The extracts were washed with water, dried and evaporated to give an oil. The oil was purified by chromatography on silica, eluting with chloroform then increasing amounts of methanol (1–15%) in chloroform to give the title product as an oily solid.

EXAMPLE 7

1-Phenylsulphonyl-1,4,5,6,7,8-hexahydro-6-methyl-8-phenylpyrrolo[2,3-d]azepine

A mixture of 1-phenylsulphonyl-1,4,5,6,7,8-hexahydro-8-phenylpyrrolo[2,3-d]azepine (1.24 g), formic acid (0.86 gm), 40% formaldehyde (1.3 ml), and dimethylformamide (30 ml) were refluxed for 1 hour. After evaporating to dryness, 5M hydrochloric acid was added to the residue and the solution was washed with ether three times. The aqueous solution was basified with 5M sodium hydroxide and the product was extracted into dichloromethane. The extracts were washed with water, dried and evaporated to give a solid, m.p. 115°–116° C. (ethanol).

EXAMPLE 8

1-Phenylsulphonyl-1,4,5,6,7,8-hexahydro-6-methyl-8-phenylpyrrolo[2,3-d]azepine

A mixture of N-(2-hydroxy-2-phenylethyl)-N-methyl-2-(1-phenylsulphonyl-3-pyrrolyl)ethylamine (5.5 g), trifluoroacetic acid (200 ml) and methanesulphonic acid (2.13 g) was refluxed for 2.5 hours. After evaporating to dryness, water then 0.880 ammonia were added and the product was extracted into dichloromethane. The extracts were washed with water, dried and evaporated to give an oil. The oil was purified by chromatography on silica, eluting with chloroform then increasing amounts of methanol (1–5%) in chloroform to give the title product as a solid, m.p. 115°–116° C. (ethanol).

EXAMPLE 9

1,4,5,6,7,8-Hexahydro-6-methyl-8-phenylpyrrolo[2,3-d]azepine

A mixture of 1-phenylsulphonyl-1,4,5,6,7,8-hexahydro-6-methyl-8-phenylpyrrolo[2,3-d]azepine (0.48 g), 50% sodium hydroxide (25 ml) and ethanol (50 ml) was refluxed for 75 minutes. The solution was evaporated to half its original volume, diluted with water and the product was extracted into dichloromethane. The extracts were washed with water, dried and evaporated to give an oily solid, which was chromatographed over silica, eluting with dichloromethane and increasing amounts of methanol (1-10%) in dichloromethane to give the title product as a solid, m.p. 90°-91° C. (cyclohexane).

EXAMPLE 10

2,3-Dibromo-1,4,5,6,7,8-hexahydro-6-methyl-8-phenylpyrrolo[2,3-d]azepine

A solution of 1,4,5,6,7,8-hexahydro-6-methyl-8-phenylpyrrolo[2,3-d]azepine (0.55 g) in tetrahydrofuran (10 ml) was cooled to −70° C. N-Bromosuccinimide (1.06 g) was added portionwise over 5 minutes, then the temperature was allowed to reach −10° C. over 75 minutes. Water was added and the product was extracted into ethyl acetate. The extracts were washed with water, dried and evaporated to give an oil, which was chromatographed on florisil, eluting with chloroform, 1% methanol in chloroform, and 2% methanol in chloroform to give the title compounds, m.p. 136°-137° C. (acetonitrile).

EXAMPLE 11

2-Bromo-1,4,5,6,7,8-hexahydro-6-methyl-8-phenylpyrrolo[2,3-d]azepine

A solution of 1,4,5,6,7,8-hexahydro-6-methyl-8-phenylpyrrolo[2,3-d]azepine (0.238 g) in tetrahydrofuran (30 ml) was cooled to −70° C. N-Bromosuccinimide (0.188 g) in tetrahydrofuran (3 ml) was added dropwise over 10 minutes, allowing the temperature to reach −10° C. over 40 minutes. Water was added and the product was extracted into ethyl acetate. The extracts were washed with water, dried and evaporated to give the title product as a solid, m.p. 132°-133° C. (acetonitrile).

EXAMPLE 12

3-Bromo-1,4,5,6,7,8-hexahydro-6-methyl-8-phenylpyrrolo[2,3-d]azepine

A solution of 2-bromo-1,4,5,6,7,8-hexahydro-6-methyl-8-phenylpyrrolo[2,3-d]azepine (0.1 g) in dichloromethane (5 ml) was cooled to 0° C. Trifluoroacetic acid (0.044 ml) was added and the solution was stirred for 4 hours at room temperature. After evaporating to dryness, water then 0.880 ammonia were added and the product was extracted into dichloromethane. The extracts were washed with water, dried and evaporated to give an oily solid, which was purified by chromatography over florisil, eluting with chloroform, 1% methanol in chloroform, and then 2% methanol in chloroform to give the title compound as an oil. $\delta$H [300 MHz; CDCl$_3$] 7.23–7.41 (5H,m,Ph), 6.51 (1H,s,2H), 4.25 (1H,dd,8-H), 2.63–3.06 (6H,m,3CH$_2$), 2.50 (3H,s,NMe). MS m/z 305/307.

The following Examples illustrate the preparation of typical formulations containing an active ingredient according to the invention.

EXAMPLE 13

Hard gelatin capsule

Each capsule contains

| Active ingredient | 10 mg |
|---|---|
| 1% Silicone starch | 250 mg |

The active ingredient is blended with the 1% silicone starch and the formulation is filled into gelatin capsules.

EXAMPLE 14

Tablet

Each capsule contains

| Active ingredient | 10 mg |
|---|---|
| Calcium carbonate | 300 mg |
| Magnesium stearate | 10 mg |
| Starch | 30 mg |
| Hydroxypropylmethyl cellulose | 10 mg |
| Iron oxide | 4 mg |

The active ingredient is granulated with calcium carbonate and starch. The dried granulate is blended with lubricant and disintegrant and compressed into tablets of the required dosage strength. The tablet may then be coated.

EXAMPLE 15

Injection

| Active ingredient | 10 mg |
|---|---|
| Water | 1 mg |

The active ingredient is dissolved in water and distributed into vials, ampoules or pre-pack syringes using appropriate equipment. The product is sterilised.

We claim:

1. A compound of the formula

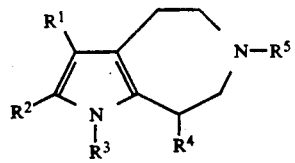

in which $R^1$ and $R^2$ are each hydrogen, halo, hydroxy, nitro, $C_{1-4}$ alkylcarbonyl, or hydroxy-$C_{1-4}$ alkyl; $R^3$ is hydrogen or phenylsulfonyl; $R^4$ is phenyl, benzofuranyl, dihydrobenzofuranyl or substituted phenyl wherein from 1 to 3 phenyl substituents may be independently selected from the group consisting of nitro, cyano, amino, hydroxyl, trifluoromethyl, $C_{1-4}$ alkyl, fluoro, chloro, bromo, and $C_{1-4}$ alkoxy; $R^5$ is hydrogen or $C_{1-4}$ alkyl; or an acid addition salt thereof.

2. A compound according to claim 1, in which $R^1$ and $R^2$ are each hydrogen or halo.

3. A compound according to claim 2, in which $R^3$ is hydrogen, and provided that $R^1$ and $R^2$ are not both hydrogen.

4. A compound according to claim 3, in which $R^4$ is phenyl substituted with $C_{1-4}$ alkyl, $C_{1-4}$ alkoxy or halogen.

5. A pharmaceutical formulation comprising a compound according to claim 1 provided that $R^1$ and $R^2$ are not both hydrogen, and $R^3$ is hydrogen, or a pharmaceutical salt thereof, together with a pharmaceutical diluent or carrier therefor.

6. A method of treating an mammal, including a human, suffering from or susceptible to a disease associated with the $D_1$ dopamine receptor which comprises administering an effective amount of a compound according to claim 1 provided that $R^1$ and $R^2$ are not both hydrogen, and $R^3$ is hydrogen, or a pharmaceutical salt thereof.

7. A method of claim 6 wherein the $D_1$ associated disease is selected from the group consisting of depression, parkinsonism, mild anxiety states, and psychotic conditions.

8. A method of claim 7 wherein the $D_1$ associated disease is a psychotic condition selected from the group consisting of schizophrenia and acute mania.

* * * * *